United States Patent [19]

Perregaard

[11] Patent Number: 4,525,360

[45] Date of Patent: Jun. 25, 1985

[54] ANTI-PSYCHOTIC PHENYLINDENE DERIVATIVES AND ACID ADDITION SALTS THEREOF

[75] Inventor: Jens K. Perregaard, Olstykke, Denmark

[73] Assignee: Kefalas A/S, Copenhagen, Denmark

[21] Appl. No.: 539,308

[22] Filed: Oct. 5, 1983

[30] Foreign Application Priority Data

Oct. 7, 1982 [GB] United Kingdom ............... 8228729

[51] Int. Cl.$^3$ ................. A61K 31/44; A61K 31/445; C07D 401/06; C07D 211/08
[52] U.S. Cl. ................................. 514/277; 514/340; 546/205; 546/206; 546/277; 546/278; 546/330; 546/339; 546/344; 546/348; 546/350; 514/341; 514/342; 514/357
[58] Field of Search ............... 546/205, 206, 277, 278, 546/330, 339, 344, 348, 350; 424/263, 267

[56] References Cited

U.S. PATENT DOCUMENTS 3,476,759 11/1969 Paragamian .................. 546/205 X
3,644,372  2/1972 Paragamian .................... 546/205

Primary Examiner—Richard A. Schwartz
Attorney, Agent, or Firm—Gordon W. Hueschen

[57] ABSTRACT

The present invention relates to novel phenylindene derivatives having interesting pharmacodynamic properties which make them useful as psychopharmacologicals in the treatment especially of psychoses such as schizophrenia, having a low degree of undesired side effects such as cataleptic effects, methods for the preparation of said phenylindene derivatives, pharmaceutical compositions containing same, and methods for the treatment of psychic disorders, such as psychoses and depressions and pain, by administering a therapeutically active amount of one of said derivatives to a living animal body, including human beings.

12 Claims, No Drawings

ANTI-PSYCHOTIC PHENYLINDENE DERIVATIVES AND ACID ADDITION SALTS THEREOF

SUMMARY OF THE INVENTION

The novel 3-phenyl-indene-1 or 3-phenylidene-2 derivatives of the present invention are represented by the following formula:

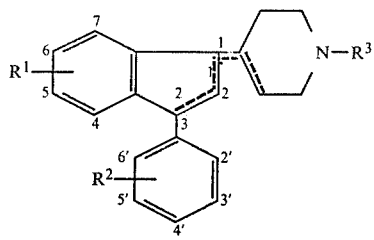
I wherein the other dotted lines indicate optional bonds;

$R^1$ is hydrogen, halogen, lower alkyl, lower alkoxy, hydroxymethyl, lower alkoxymethyl, cyano, trifluoromethyl, lower alkylthio or lower alkylsulfonyl;

$R^2$ is halogen, lower alkyl or trifluoromethyl; and $R^3$ is hydrogen, alkyl or alkenyl (straight or branched chain with $C_1$-$C_6$ inclusive) optionally substituted with one or two hydroxy groups, any hydroxy group present being optionally esterified with an aliphatic carboxylic acid having from two to twenty-four carbon atoms inclusive, or $R^3$ is

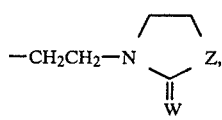

wherein Z is $NR^4$, O or S, where $R^4$ is H or lower alkyl, and W is O or S, as well as pharmaceutically acceptable acid addition salts of the compounds of Formula I.

The novel phenylindene derivatives are potent dopaminergic antagonists both in vivo and in vitro pharmacological tests as compared to classical neuroleptics. In addition, most of the indenes of Formula I are strong 5-HT antagonists both perifically and centrally, which might be a benefit in the treatment of psychic disorders or cardiovascular diseases.

BACKGROUND OF THE INVENTION

Recently some 1-piperazino-3-phenylindanes have been described as having neuroleptic activity (see European Patent Application No. 81300785.3).

The terms "lower alkyl" and "lower alkoxy" mean alkyl or alkoxy having from one to four carbon atoms inclusive, straight or branched, among which may be mentioned methyl, ethyl, propyl, iso-propyl, butyl, sec-butyl, methoxy, ethoxy, iso-propoxy or n-butoxy.

This invention also includes pharmaceutically acceptable salts of the compounds of Formula I formed with non-toxic organic acids. Such salts are easily prepared by methods known to the art. The base is reacted with either the calculated amount of organic or inorganic acid in a aqueous miscible solvent, such as acetone or ethanol, with isolation of the salt by concentration and cooling or an excess of the acid in aqueous immiscible solvent, such as ethyl ether or chloroform, with the desired salt separating directly.

Exemplary of such organic salts are those with maleic, fumaric, benzoic, ascorbic, embonic, succinic, oxalic, bis-methylene-salicylic, methanesulfonic, ethanedisulfonic, acetic, propionic, tartaric, salicylic, citric, gluconic, lactic, malic, mandelic, cinnamic, citraconic, aspartic, stearic, palmitic, itaconic, glycolic, p-aminobenzoic, glutamic, benzene sulfonic and theophylline acetic acids, as well as the 8-halotheophyllines, for example 8-bromo-theophylline.

Exemplary of such inorganic salts are those with hydrochloric, hydrobromic, sulfuric, sulfamic, phosphoric and nitric acids. Of course, these salts may also be prepared by the classical method of double decomposition of appropriate salts, which is wellknown to the art. The compounds of Formula I as well as the pharmaceutically acceptable acid addition salts thereof may be administered both orally and parenterally, for example in the form of tablets, capsules, powders, syrups or solutions for injection.

Of the phenyl-indenes of Formula I those wherein $R^1$ is fluorine, $CF_3$, chlorine or methyl in the 6-position, $R^2$ is fluorine in the 4'-position, and $R^3$ is methyl, 2-hydroxyethyl or

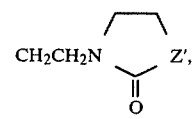

wherein Z' is NH or O, have the most prominent antipsychotic activity.

According to the method of the invention the compounds of Formula I are prepared by (a) dehydrating a compound of the formula:

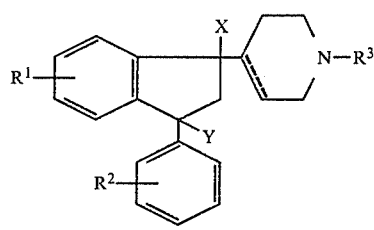
II wherein $R^1$, $R^2$ and $R^3$ are as defined above, X and Y are hydrogen or hydroxy, X being hydroxy when Y is hydrogen and vice versa, or (b) treating a compound of the formula:

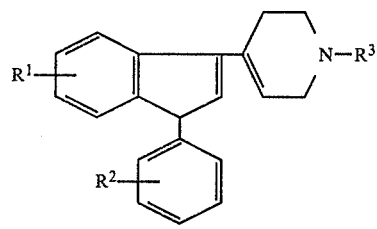

wherein $R^1$, $R^2$ and $R^3$ are as defined above with an acid or base, or by heating to cause migration of the double bonds in order to obtain a compound of Formula I of the formula:

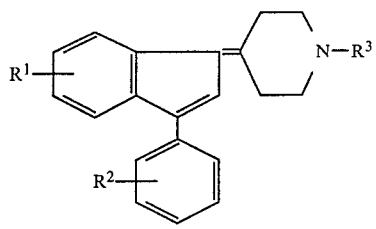

wherein R¹, R² and R³ are as defined above, or (c) heating an acid addition salt of a compound of the formula:

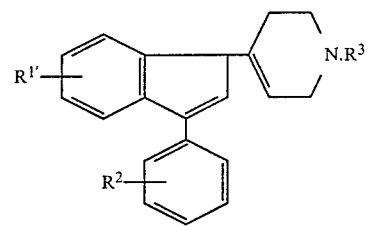

wherein R² and R³ are as defined above and R¹' is lower alkyl, lower alkoxy, hydroxymethyl, alkoxymethyl or lower alkylthio, to cause migration of one double bond to a compound of Formula I of the formula:

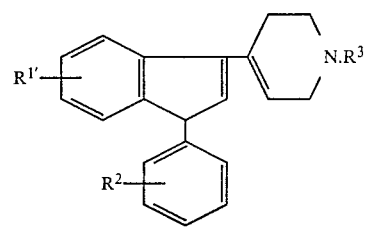

wherein R¹', R² and R³ are as defined above or (d) treating a compound of the formula:

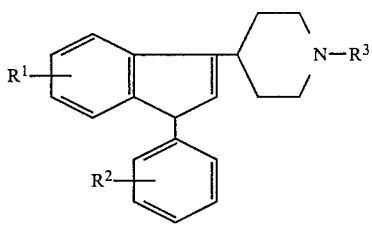

wherein R¹, R² and R³ are as defined above, with a base to cause migration of the double bond in order to obtain a compound of the formula:

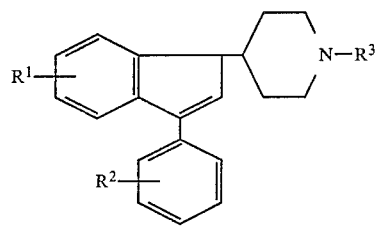

or (e) reacting a compound of the following formula:

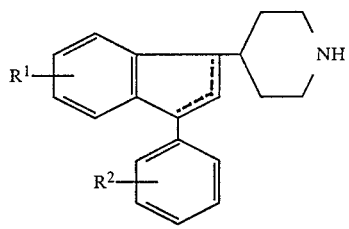

wherein R¹ and R² are as defined above, with a compound of the formula R³X wherein R³ is as defined above and X is halogen or an epoxide of formula

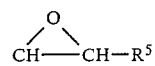

wherein R⁵ is lower alkyl or hydroxyalkyl, whereupon the compound of Formula I is isolated as the free base or a pharmaceutically acceptable acid addition salt thereof and, in the case where one or two hydroxy groups are present, if desired, reacting the compound of Formula I with a reactive derivative of an aliphatic carboxylic acid having from 2 to 24 carbon atoms inclusive, and isolating the ester formed as the free base or an acid addition salt thereof.

The intermediates of Formula II, wherein X is hydroxy and Y is hydrogen, may conveniently be prepared according to the following scheme:

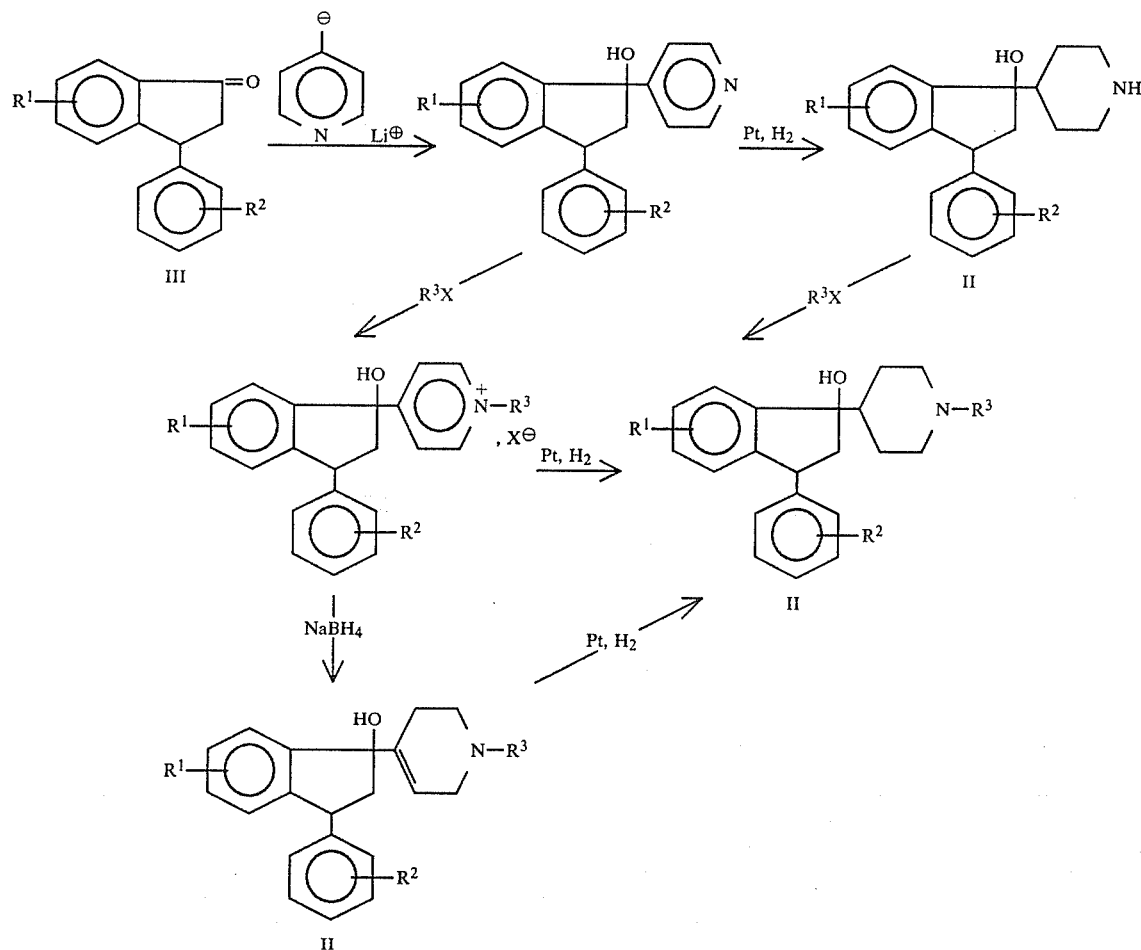
wherein $R^1$, $R^2$ and $R^3$ are as defined above.
The 3-phenylindanones (III) were synthesized according to methods well-known from the litterature.
Intermediates of Formula II, wherein X is hydrogen and Y is hydroxy, may conveniently be prepared from 3-pyridyl-indanones (IV) according to the following reaction scheme:
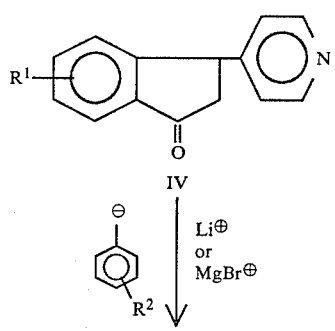

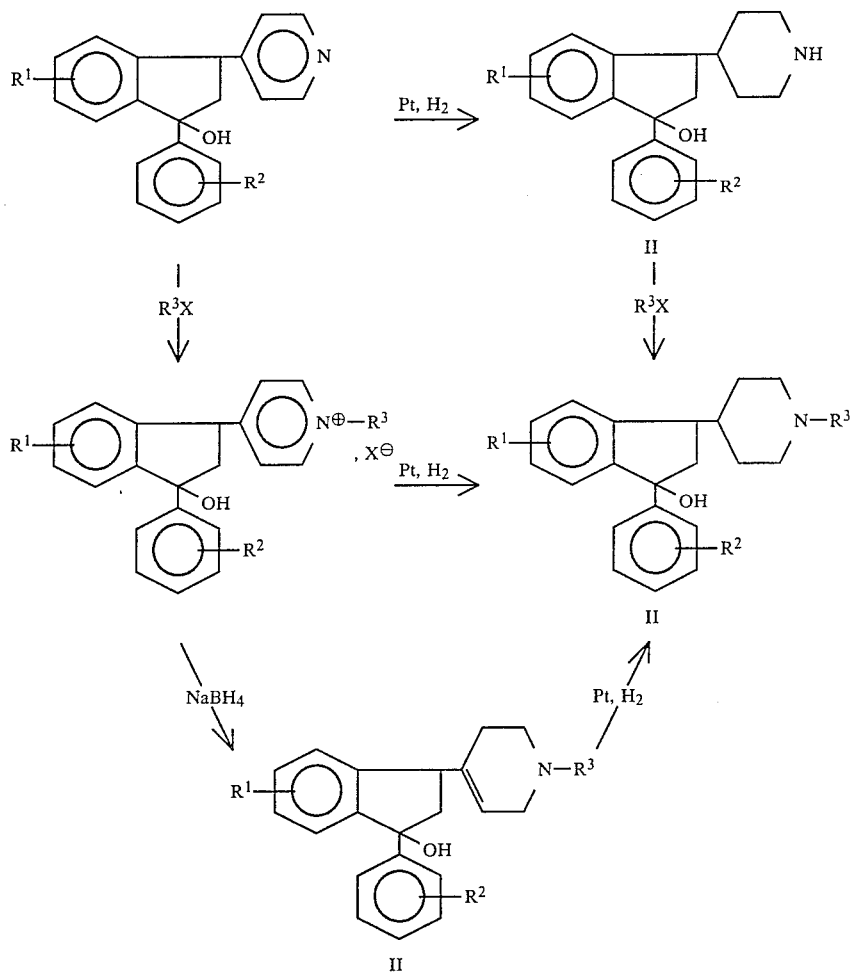

of from 3-piperidylindanones according to the following scheme:

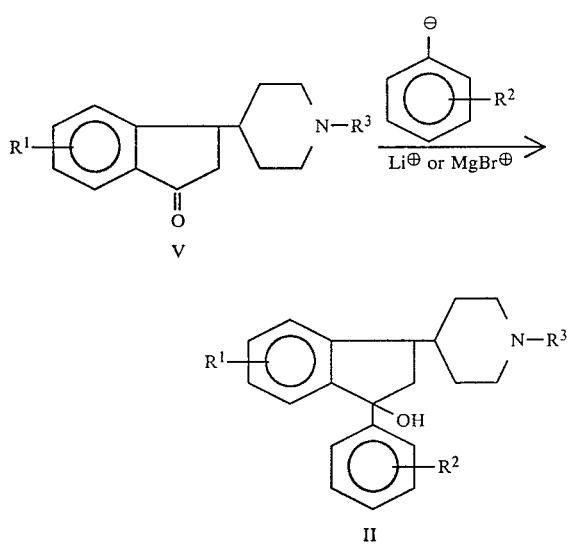

The substituents $R^1$, $R^2$ and $R^3$ in these schemes are as defined above.

The 3-pyridylindanones (IV) and 3-piperidylindanones (V) were prepared according to methods described in the litterature (J. Med. Chem., 11, (1968), 1064–1066).

The dehydration of the compound II according to method variant (a) of the invention is conveniently carried out such as by hydrogen chloride or hydrogen bromide in an inert organic solvent, or by anhydrous trifluoroacetic acid. The reaction temperature is preferably kept low or near 50 degrees Centigrade.

The rearrangement according to method (b) may be carried out in aqueous media with strong mineral acids or strong alkalihydroxides, or by heating a salt in an organic solvent at a temperature of about 100 degrees Centigrade.

In method (c) the heating is preferably carried out in the presence of an inert solvent such as dimethyl-sulfoxide at about 100 degrees Centigrade.

In method (d) the migration of the double bond takes place in a strongly alkaline aqueous medium, such as sodium hydroxide solution.

The optional esterification of any hydroxy group or groups present in the compound of Formula I may, according to the invention, conveniently be carried out by a reactive derivative of the carboxylic acid having from two to twenty-four carbon atoms inclusive, such as an acid chloride or anhydride. As carboxylic acids may be mentioned acetic acid, propionic acid, valeric acid, decanoic acid, palmitic acid and behenic acid.

The methods of the invention shall be illustrated by the following examples, which may not be construed limiting:

EXAMPLE 1

3-(4'-Fluorophenyl)-1-hydroxy-6-methyl-1-pyrid-4-ylindane.

4-Bromopyridine (49 g) dried overnight by anh.K$_2$CO$_3$ in 500 ml of dry ether was cooled below −60° C. and kept under dry N$_2$. 188 ml 15% W/V n-butyllithium in h-hexane were added dropwise in 15 min. The temperature was kept below −40° C., and 70 g of 3-(4'-fluoro-phenyl)-6-methyl-1-indanone in 500 ml of dry ether were added within a few minutes. The temperature was slowly allowed to reach room temperature. The reaction mixture was poured onto 1 L of crushed ice and 100 g of NH$_4$Cl. The mixture was stirred under ice cooling for 2 hours and the precipitate filtered off yielding 38 g (41%) of the title compound. MP: 196°–199° C. The organic phase was separated and stirred with 100 ml ice cold 2M hydrochloric acid. The hydrochloride precipitated and was filtered off. Yield: 10.4 g (10.1%). MP: 208°–209° C. The total yield was thus 51.1%. From the organic phase was recovered 19.8 g (28.3%) of the starting indanone.

In a corresponding manner the following 1-pyridylindanes were prepared:

| | | MP (°C.) | |
|---|---|---|---|
| R$^1$ | R$^2$ | base | hydrochloride |
| 6-F | 4'-F | 206 | 210-11 (dec.) |
| 6-CH$_3$O | 4'-F | 182–85 | |
| 6-CF$_3$ | 4'-F | 216–18 | |
| 6-Cl | 4'-F | 208–10 | |
| 6-(2-propyl) | 4'-F | 211–13 | |
| H | 4'-F | 205–08 | 215–17 |

EXAMPLE 2

3-(4'-Fluorophenyl)-1-hydroxy-6-methyl-1-(1-methyl-1,2,3,6-tetrahydropyrid-4-yl)indane. (Lu 19-131).

To 3-(4'-fluorophenyl)-1-hydroxy-6-methyl-1-pyrid-4-ylidane (10.0 g), dissolved in 100 ml of acetone, 5 ml of methyliodide were added and the solution refluxed for 1 h. After cooling the solvent was evaporated and the remaining viscous oil dissolved in 100 ml of methanol. The solution was ice cooled, and NaBH$_4$ (3.0 g) was added over a period of 1 h. The resulting suspension was finally stirred for another ½ hour at room temperature, poured into 50 g NH$_4$Cl in 1 L of H$_2$O and extracted with ethylacetate (2×150 ml). The combined organic phases were dried (anh.K$_2$CO$_3$), evaporated and the remaining crude product washed with isopropylether. Yield: 8.1 g (77%) of title compound. MP: 176°–78° C.

EXAMPLE 3

6-Fluoro-3-(4'-fluorophenyl)-1-hydroxy-1-(4-piperidyl)indane. (Lu 19-139).

6-Fluoro-3-(4'-fluorophenyl)-1-hydroxy-1-pyrid-b 4-ylidane, hydrochloride (5.0 g) was dissolved in 200 ml of methanol, 0.5 g of PtO$_2$ added. The indane was hydrogenated at 3.0–3.5 atm. for 2 hrs., the catalyst subsequently filtered off and the methanol evaporated. Ice-cold NaOH solution (100 ml 0.2M) was added to the residue and the resulting base extracted with ethyl acetate (2×50 ml). The combined organic phases were dried (MgSO$_4$) and the solvent evaporated. The crude crystalline product was stirred with ice cooled isopropylether (25 ml) and filtered off. Yield: 3.8 g (83.2%) of the title compound. MP: 198° C.

EXAMPLE 4

6-Fluoro-3-(4'-fluorophenyl)-1-hydroxy-1-(1-methyl-4-piperidyl)-indane.

6-Fluoro-3-(4'-fluorophenyl)-1-hydroxy-1-pyrid-4-ylindane (5.0 g) was reacted with methyliodide as described in Example 2, and the resulting pyridylium iodide (viscous oil) was dissolved in ethanol (150 ml) and 0.5 g PtO$_2$ added. The estimated amount of hydrogen was consumed in 3 hrs. (3.0–3.5 atm.). The catalyst was filtered off and the ethanol evaporated. Ice-cold NaOH solution (100 ml 0.2M) was added to the residue and the resulting base extracted with ethyl acetate (2×50 ml). The combined organic phases were dried (MgSO$_4$) and the solvent evaporated. The remaining oil was dissolved in isopropylether, and by cooling the product precipitated and was filtered off. Yield: 4.7 g (88.8%) of the title compound. MP: 146°–147° C.

EXAMPLE 5

3-(4'-Fluorophenyl)-1-hydroxy-1-(1-hydroxyethyl-1,2,3,6-tetrahydropyrid-4-yl)-6-methylindane. (Lu 19-154).

3-(4'-fluorophenyl)-1-hyroxy-6-methyl-1-pyrid-4-ylindane (12.0 g) was refluxed with ethyl bromoacetate (7.5 g) in acetone (100 ml) for 4 hrs. The reaction mixture was cooled in a refrigerator over night and the precipitate filtered off. Yield: 16.8 g (91.9%) of the pyridiniumbromide. MP: 196°–198° C. (dec.). The bromide (15.0 g) was dissolved in methanol (150 ml), and ice cooled, NaBH$_4$ (5.0 g) was added during a period of 1 h. The reaction mixture was finally stirred for another ½ h at room temperature and subsequently poured into NH$_4$Cl (25 g) in 1 L of H$_2$O. The H$_2$O phase was extracted with ethyl acetate (2×200 ml), the combined organic phases dried (MgSO$_4$) and the solvent evaporated yielding 11.7 g (92.7%) of 1-(1-ethylcarboxymethyl-1,2,3,6-tetrahydropyrid-4-yl)-3-(4'-fluorphenyl)-1-hydroxy-6-methylindane. MP: 119°–20° C.

This ethyl ester (11.0 g) was dissolved in dry tetrahydrofuran (50 ml) and added dropwise to a suspension of LiAlH$_4$ (3.5 g) in dry tetrahydrofuran (150 ml) under ice cooling. The mixture was refluxed for 2 hrs., hydrolysed by careful addition of H$_2$O (10 ml) in tetrahydrofuran (200 ml). The precipitate was filtered off and the solvent evaporated. The remaining oil was dissolved in ether (25 ml), and isopropylether (75 ml) was added. By cooling the title compound precipitated. Yield: 9.7 g (98.3%). MP: 156°–57° C.

EXAMPLE 6

3-(4'-Fluorophenyl)-1-hydroxy-1-(2-imidazolidinon-1-ylethyl)-4-piperidyl)-6-methylindane.

3-(4'-Fluorophenyl)-1-hydroxy-1-(4-piperidyl)-6-methylidene (3.0 g), KI (0.2 g), K$_2$CO$_3$ (3.0 g) and 1-chloroethyl-2-imidazolidinon (1.5 g) were refluxed in methyl isobutyl ketone (50 ml) for 16 hours. The reaction mixture was poured into H$_2$O (200 ml). The phases were separated, and the organic phase was dried (MgSO$_4$) and the solvent was evaporated. By addition of cooled ether the product crystallized, yielding 2.9 g (82.1%) of the title compound. MP: 176°–177° C.

In corresponding manners to the Examples 2–6 the following 1-hydroxy-1-piperidylindanes and 1-hydroxy-1-(tetrahydropyridyl)indanes were prepared:

3-(4'-Fluorophenyl)-1-hydroxy-(1-hydroxyethyl-4-piperidyl)-6-methylindane, oil.

3-(4'-Fluorophenyl)-1-hydroxy-6-methyl-1-(1-methyl-4-piperidyl)indane. MP: 135° C.

6-Fluoro-3-(4'-fluorophenyl)-1-hydroxy-1-(1-methyl-1,2,3,6-tetrahydropyrid-4-yl)indane. MP: 180°–183° C.

3-(4'-Fluorophenyl)-1-hydroxy-1-(1-hydroxyethyl-1,2,3,6-tetrahydropyrid-4-yl)-6-methoxy-indane. MP: 60°–70° C. (amorph.).

3-(4'-Fluorophenyl)-1-hydroxy-1-(1-hydroxyethyl-4-piperidyl)-6-methoxyindane, oil.

3-(4'-Fluorophenyl)-1-hydroxy-1-(1-hydroxyethyl-1,2,3,6-tetrahydropyrid-4-yl)-6-yl)-6-trifluoromethylindane, oil.

3-(4'-Fluorophenyl)-1-hydroxy-1-(1-methyl-4-piperidyl)-6-trifluoromethylindane, MP: 161°–163° C.

3-(4'-Fluorophenyl)-1-hydroxy-1-(1-methyl-1,2,3,6-tetrahydropyrid-4-yl)-6-chlorindane, oil.

3-(4'-Fluorophenyl)-1-hydroxy-1-(1-methyl-1,2,3,6-tetrahydropyrid-4-yl)-6-(2-propyl)indane, MP: 159° C.

3-(4'-Fluorophenyl)-1-hydroxy-1-(1-hydroxyethyl-4-piperidyl)-6-(2-propyl)indane, oil.

3-(4'-Fluorophenyl)-1-hydroxy-1-(1-(2-imidazolidinon-1-ylethyl)-4-piperidyl)indane, MP: 172°–179° C.

3-(4'-Fluorophenyl)-1-hydroxy-1-(1-(2-oxazolidinon-3-ylethyl)-4-piperidyl)-6-methylindane, MP: 137°–140° C. (maleate).

3-(4'-Fluorophenyl)-1-hydroxy-1-(1-(2-imidazolidinon-1-ylethyl)-4-piperidyl)-6-fluoridane, oil.

EXAMPLE 7

3-(4'-Fluorophenyl)-6-methyl-1-(1-methyl-1,2,3,6-tetrahydropyrid-4-yl)-1-indene, hydrobromide. (Lu 20-041)

3-(4'-Fluorophenyl)-1-hydroxy-6-methyl-1-(1-methyl-1,2,3,6-tetrahydropyrid-4-yl)indane, (prepared as in Example 2) (4 g) was added to ice cooled acetone (25 ml) containing anh.HBr (1.5 g). The precipitated hydrobromide was filtered off and washed with dry ether. Yield: 4.5 g (95%) of the title compound. MP: 262° C. (dec.).

In a corresponding manner the following indenes were prepared:

3-(4'-Fluorophenyl)-1-(1-hydroxyethyl-1,2,3,6-tetrahydropyrid-4-yl)-6-methyl-1-indene, hydrobromide. MP: 234°–235° C. (Lu 19-153)

6-Fluoro-3-(4'-fluorophenyl)-1-(1-methyl-1,2,3,6-tetrahydropyrid-4-yl)-1-indene, hydrobromide. MP: 288°–290° C. (Lu 20-025)

6-Fluoro-3-(4'-fluorophenyl)-1-(1-hydroxyethyl-1,2,3,6-tetrahydropyrid-4-yl)-1-indene, hydrobromide. MP: 194°–196° C. (Lu 19-157)

3-(4'-Fluorophenyl)-1-(1-hydroxyethyl-1,2,3,6-tetrahydropyrid-4-yl)-6-methoxy-1-indene, hydrobromide. MP: 166°–168° C. (Lu 20-021)

3-(4'-Fluorophenyl)-1-(1-hydroxyethyl-1,2,3,6-tetrahydropyrid-4-yl)-6-trifluoromethyl-1-indene, hydrobromide. MP: 153°–154° C. (Lu 20-004)

3-(4'-Fluorophenyl)-1-(1-methyl-4-piperidyl)-6-trifluoromethyl-1-indene, hydrobromide. MP: 163.5° C. (Lu 20-071)

6-Chloro-3-(4'-fluorophenyl)-1-(1-methyl-1,2,3,6-tetrahydropyrid-4-yl)-1-indene, hydrobromide. MP: 292°–294° C. (Lu 20-079)

3-(4'-Fluorophenyl)-1-(1-methyl-1,2,3,6-tetrahydropyrid-4-yl)-6-(2-propyl)-1-indene, hydrobromide. MP: 177°–178° C. (Lu 20-099)

EXAMPLE 8

3-(4'-Fluorophenyl)-1-(1-hydroxyethyl-4-piperidyl)-6-methyl-1-indene, hydrochloride. (Lu 20-008).

3-(4'-Fluorophenyl)-1-hydroxy-1-(1-hydroxyethyl-4-piperidyl)-6-methylindane (5.6 g) was dissolved in 2-propanol (25 ml), and 2 ml of anh. trifluoroacetic acid was added. The mixture was gently heated (40°–50° C.) for a short while. Ether (25 ml) was added and the solution cooled on an ice bath. Dry HCl gas was bubbled through, and the precipitate filtered off.

Yield: 3.2 g (54.4%) of the title compound. MP: 216°–218° C.

EXAMPLE 9

3-(4'-Fluorophenyl)-1-(1-(2-imidazolidinon-1-ylethyl)-4-piperidyl)-6-methyl-1-indene, oxalate. (Lu 20-064).

3-(4'-Fluorophenyl)-1-hydroxy-1-(1-(2-imidazolidinon-1-ylethyl)-4-piperidyl)-6-methylindane (1.8 g) was stirred in 10 ml of anh. $CF_3COOH$ for ½ h. at room temperature. Oxalic acid (0.6 g) was added and the reaction mixture was evaporated 3 times with 2-propanol. The mixture was left stirring overnight with 10 ml of 2-propanol and the precipitate subsequently filtered off, yielding 1.4 g (49.6%) of the title compound. MP: 199°–200° C.

In a corresponding manner, as indicated in Examples 7–9, the following piperidyl indenes were prepared:

3-(4'-Fluorophenyl)-6-methyl-1-(1-methyl-4-piperidyl)-1-indene, hydrobromide. MP: 204°–206° C. (Lu 20-048).

6-Fluoro-3-(4'-fluorophenyl)-1-(1-methyl-4-piperidyl)-1-indene, hydrobromide. MP: 214°–215° C. (Lu 20-028).

6-Fluoro-3-(4'-fluorophenyl)-1-(1-hydroxyethyl)-4-piperidyl)-1-indene, hydrochloride. MP: 217°–219° C. (Lu 19-158).

6-Fluoro-3-(4'-fluorophenyl)-1-(4-piperidyl)-1-indene, hydrochloride. MP: 285°–288° C. (Lu 19-140)

3-(4'-Fluorophenyl)-1-(1-hydroxyethyl-4-piperidyl)-6-methoxy-1-indene, hydrobromide. MP: 180°–185° C. (Lu 20-033).

3-(4'-Fluorophenyl)-1-(1-hydroxyethyl-4-piperidyl)-6-(2-propyl)-1-indene, hydrochloride. MP: 179°–180° C. (Lu 20-109)

6-Fluoro-3-(4'-fluorophenyl)-1-(1-(2-imidazolidinon-1-ylethyl)-4-piperidyl)-1-indene 6-Fluoro-3-(4'-fluorophenyl)-1-(1-(2-imidazolidinon-1-ylethyl)-4-piperidyl)-1-indene, oxalate. MP: 209°–211° C. (Lu 20-087)

3-(4'-Fluorophenyl)-1-(1-(2-imidazolidinon-1-ylethyl)-4-piperidyl)-1-indene, oxalate. MP: 164°–165° C. (Lu 20-078)

3-(4'-Fluorophenyl)-6-methyl-1-(1-(2-oxazolidinon-3-ylethyl)-4-piperidyl)-1-indene, trifluoroacetate. MP: 166°–167° C. (Lu 21-002)

EXAMPLE 10

3-(4'-Fluorophenyl)-3-hydroxy-6-methyl-1-(4-pyridyl)indane

4-Bromofluorobenzene (87.5 g) dissolved in 1000 ml of dry ether was cooled to −20° C. and kept under dry $N_2$. N-butyllithium (0.5 moles 15% W/V in n-hexane) was added during 1 hour while the temperature was kept below 0° C. The reaction mixture was stirred for another ½ h and further cooled to −30° C. 5-Methyl-3-pyridylindanone (75 g) (prepared according to the standard methods—J. Med. Chem., 11, (1968), 1064–1066) dissoled in dry ether (500 ml) was added dropwise at such a rate as to keep the temperature below −10° C. Subsequently the temperature was slowly raised to room temperature and the mixture poured into $NH_4Cl$(100 g) in $H_2O$ (3 liters). The organic phase was separated and washed with brine, dried ($MgSO_4$), and the solvents evaporated. Upon addition of ether (200 ml) the title compound precipitated and was filtered off. Yield: 55 g (52%). MP: 187°–192° C.

In a corresponding manner was prepared:
3-(4'-Fluorophenyl)-3-hydroxy-4-methyl-1-(4-pyridyl)indane. MP: 234°–237° C.

EXAMPLE 11

3-(4'-Fluorophenyl)-3-hydroxy-1-(1-hydroxyethyl-1,2,3,6-tetrahydropyrid-4-yl)-6-methylindane 3-(4'-Fluorophenyl)-3-hydroxy-6-methyl-1-(4-pyridyl)indane (Example 8) (9.0 g) was refluxed with ethyl bromoacetate (5.0 g) in acetone (50 ml) for 3 hrs. The reaction mixture was cooled in a refrigerator overnight and the precipitated pyridinium bromide filtered off. Yield: 7.8 g (56.9%). MP: 177°–78° C. This bromide (7.0 g) was dissolved in methanol (50 ml), cooled to 0° C., and $NaBH_4$ (3.0 g) was added during 1 hour under stirring. The reaction mixture was poured into $NH_4Cl$ (10 g) in 1 liter of $H_2O$ and finally extracted with ethyl acetate (2×150 ml). The combined organic phases were dried ($MgSO_4$) and the ethyl acetate evaporated. The remaining oil (1-(1-ethylcarboxymethyl-1,2,3,6-tetrahydropyrid-4-yl)-3-(4'-fluorophenyl)-3-hydroxy-6-methylindane) was dissolved in dry tetrahydrofuran (25 ml) and added dropwise to a suspension of $LiAlH_4$ (1.8 g) in dry tetrahydrofuran under ice cooling. The mixture was refluxed for two hours, hydrolysed by careful addition of $H_2O$ (5 ml) in tetrahydrofuran (100 ml). The precipitate was filtered off, and the solvent evaporated leaving the title compound as an oil.

In a corresponding manner the following 3-hydroxy-1-(tetrahydropyridyl)indanes were prepared:
3-(4'-Fluorophenyl)-3-hydroxy-6-methyl-1-(1-methyl-1,2,3,6-tetrahydropyrid-4-yl)indane, oil.
3-(4'-Fluorophenyl)-3-hydroxy-1-(1-hydroxyethyl-1,2,3,6-tetrahydropyrid-4-yl)-4-methylindane. MP: 144°–145° C.

EXAMPLE 12

3-(4'-Fluorophenyl)-3-hydroxy-1-(1-hydroxyethyl)-4-piperidyl)-6-methylindane 3-(4'-Fluorophenyl)-3-hydroxy-1-(1-hydroxyethyl-1,2,3,6-tetrahydropyrid-4-yl)-6-methylindane (Example 9) (2.0 g) was dissolved in ethanol (100 ml), oxalic acid (0.7 g) and $PtO_2$ (0.3 g) were added. The compound was hydrogenated at 3.2 atm. for 2 hours. The catalyst was filtered off and the ethanol evaporated in vacuum at room temperature. The remaining oxalate was converted into the corresponding base by NaOH-solution (100 ml-0.2M) and extracted with ethyl acetate (2×50 ml). Working-up of the combined organic phases as described above yielded the title compound as an oil.

EXAMPLE 13

6-Fluoro-3-(4'-fluorophenyl)-3-hydroxy-1-(1-methyl-4-piperidyl)indane

5-Fluoro-3-(1-methyl-4-piperidyl)indanone (100 g) (prepared according to standard methods—J. Med. Chem., 11, (1968), 1064–66) in dry tetrahydrofuran (500 ml) was added dropwise to 4-fluorophenylmagnesium bromide (from 95 g of 4-bromofluorobenzene and 20 g of Mg-turnings in 500 ml of dry tetrahydrofuran). The reaction mixture was poured into $NH_4Cl$ (100 g) and crushed ice (3 L) and extracted with ether (2×300 ml). The combined organic phases were extracted with 0.5M $CH_3COOH$ (2×500 ml). The acid $H_2O$-phase was made alkaline with 2M NaOH solution and extracted with ether (2×200 ml). The combined ether-phases were worked up as above and the starting material removed by washing with light petroleum. The title compound crystallized from isopropylether. Yield: 16.5 g (11.7%). MP: 148°–150° C.

Dehydrations performed as described in Examples 6 or 7 provided the following indenes:
3-(4'-Fluorophenyl)-6-methyl-1-(1-methyl-1,2,3,6-tetrahydropyrid-4-yl)-2-indene, hydrobromide. MP: 227°–29° C. (Lu 20-040).
3-(4'-Fluorophenyl)-1-(1-hydroxyethyl-1,2,3,6-tetrahydropyrid-4-yl)-6-methyl-2-indene, hydrobromide. MP: 207°–208° C. (Lu 20-038).
3-(4'-Fluorophenyl)-1-(1-hydroxyethyl-1,2,3,6-tetrahydropyrid-4-yl)-4-methyl-2-indene, hydrobromide. MP: 221°–223° C. (Lu 20-010)
3-(4'-Fluorophenyl)-1-(1-hydroxyethyl-4-piperidyl)-6-methyl-2-indene, hydrobromide. MP: 164°–167° C. (Lu 20-039).
3-(4'-Fluorophenyl)-1-(1-hydroxyethyl-4-piperidyl)-4-methyl-2-indene, hydrochloride. MP: 194° C. (Lu 20-011)
6-Fluoro-3-(4'-fluorophenyl)-1-(1-methyl-4-piperidyl)-2-indene. MP: 75° C. (Lu 19-004)

EXAMPLE 14

6-Fluoro-3-(4'-fluorophenyl)-1-(1-(2-imidazolidinon-1-ylethyl)-4-piperidyl)-2-indene (Lu 20-053)

6-Fluoro-3-(4'-fluorophenyl)-1-(1-(2-imidazolidinon-1-ylethyl)-4-piperidyl)-1-indene, oxalate (4.0 g) was stirred at 30° C. with 100 ml 2M NaOH solution and 25 ml of ether for 16 hours. The mixture was subsequently cooled and the precipitate filtered off, yielding 1.8 g (55%) of the title compound. MP: 172°–173° C.

In a corresponding manner the following indenes were prepared:
3-(4'-Fluorophenyl)-1-(1-hydroxyethyl-4-piperidylidenyl)-6-methyl-2-indene, hydrobromide. MP: 272°–274° C. (Lu 20-044).
6-Fluoro-3-(4'-fluorophenyl)-1-(1-methyl-4-piperidylidenyl)-2-indene, hydrochloride. MP: 267°–269° C. (Lu 19-151).
6-Fluoro-3-(4'-fluorophenyl)-1-(1-hydroxyethyl-4-piperidylidenyl)-2-indene, hydrochloride. MP: 280°–282° C. (dec.) (Lu 19-156).
6-Fluoro-3-(4'-fluorophenyl)-1-(4-piperidyl)-2-indene, hydrochloride. MP: 275°–277° C. (Lu 19-150).

3-(4'-Fluorophenyl)-1-(1-(2-imidazolidinon-1-ylethyl)-4-piperidyl)-2-indene. MP: 161°–162° C. (Lu 20-082).

EXAMPLE 15

6-Fluoro-3-(4'-fluorophenyl)-1-(1-methyl-4-piperidyl)-2-indene. (Lu 19-004)

6-Fluoro-3-(4'-fluorophenyl)-1-(4-piperidyl)-2-indene, hydrochloride (5.0 g) and $K_2CO_3$ (4.5 g) were refluxed in acetone (100 ml) for 15 min. Methyliodide (2.5 g) was added, and the mixture was stirred for another 4 h at 40° C. 500 ml of $H_2O$ were added, and the mixture was extracted with ether (2×150 ml). The combined organic phases were dried ($MgSO_4$) and the solvents evaporated. The title compound crystallized from isopropylether. Yield: 4.2 g (89.8%). MP: 75° C.

EXAMPLE 16

6-Fluoro-3-(4'-fluorophenyl)-1-(1-methyl-4-piperidylidenyl)-2-indene, hydrochloride (Lu 19-151)

6-Fluoro-3-(4'-fluorophenyl)-1-hydroxy-1-(1-methyl-1,2,3,6-tetrahydropyrid-4-yl)indane (6.0 g) was refluxed in 100 ml of a 1:1 mixture of acetic acid and concentrated hydrochloric acid for 2.5 h. The solvents were evaporated, and the remaining hydrochloride of the title compound was crystallized from 2-propanol. Yield: 2.0 g (32%). MP: 267°–269° C.

EXAMPLE 17

3-(4'-Fluorophenyl)-1-(1-hydroxyethyl-1,2,3,6-tetrahydropyrid-4-yl)-6-methyl-1-indene,hydrobromide. (Lu 19-153).

3-(4'-Fluorophenyl)-1-(1-hydroxyethyl-1,2,3,6-tetrahydropyrid-4-yl)-6-methyl-2-indene,hydrobromide (0.5 g) was heated in anh. dimethylsulfoxide (5 ml) at 100° C. for 1.5 h. The mixture was cooled to room temperature and poured under stirring into dry ether (100 ml). The precipitated title compound was filtered off. Yield: 0.45 g (90%). MP: 232°–234° C. $^1$H-NMR confirmed the migration of the double bond.

EXAMPLE 18

1-(1-decanoyloxyethyl-4-piperidyl)-6-fluoro-3-(4'-fluorophenyl)-1-indene.

6-Fluoro-3-(4'-fluorophenyl)-1-hydroxy-1-(1-hydroxyethyl-4-piperidyl)indane (3.7 g) was refluxed with decanoylchlorid (1.9 g) in acetone (50 ml) for 1 hour. The mixture was cooled to room temperature, and HCl gas was bubbled through for 4 hours. The solvent was evaporated and $H_2O$ (200 ml) and ether (100 ml) added. To the ice cooled mixture was added 0.5M $K_2CO_3$ solution until pH=9. The organic phase was separated and dried ($MgSO_4$) and the ether evaporated leaving an oil which was chromatographed on silica gel (eluent 10% methanol in $CH_2Cl_2$) yielding 4.2 g (81%) of the title compound.

The novel indenes of Formula I were tested pharmacologically in standard and reliable animal tests.

When the results with salts were compared to the results obtained with the free base it was found that the effect was the same as that obtained with the equivalent amount of free base.

The tests may be described as follows:

Methylphenidate antagonism (ED50 $\mu$mol/kg i.p.)

Perspex observation cages without bottom and lid, consisting of 5 sections each measuring 12×25×30 cm. White corrugated paper.
Mice, male, 18–25 g.

Dosage and procedure

The test substance is given i.p. in the doses 0, ⅛, 1/32 and 1/128 of the determined "i.p. LD50".3×2 mice are used for each dose level. Two hours after injection of test substance, methylphenidate, 60 mg/kg, is injected s.c. After administration of methylphenidate the mice are placed in the observation cages, 2 in each cage, where they remain for exactly 1 hour. The cages are placed on corrugated paper, the corrugations facing upwards. It is examined whether the mice have been biting the corrugated paper or not. If not, the substance has had an antagonistic effect. If one or more of the control pairs have not bee biting, the test has to be repeated in a new set of mice.

The result is stated in fractions: 0/3, ⅓, ⅔ and 3/3 where 0, 1, 2 and 3 are the number of pairs which have not been biting on receipt of the dose in question.

The results are calculated as the dose ($ED_{50}$), which causes antagonism in 50% of the test animals.

Catalepsy wire mesh, rat, max. (ED50 $\mu$mol/kg p.o.)

A vertical wire netting (50 cm×49 cm). The meshes (openings) of the netting are square (1 cm×1 cm). The wire diameter is 2 mm.
Stop watch.
Rats, male, 180–200 g.

Dosage and procedure

The animals are labeled and used in groups of five. The test substance is administered orally (p.o.) at 4 dose levels selected from a fixed dose scale.

The animals are placed in the middle of the vertical wire netting 60, 120, 180, 240, 300 and 360 minutes after administration of the test compound. The animals are considered cataleptic when they remain immobile during a period of 15 seconds. This cataleptic reaction is designated +.

If the rats are "atonic" and passively slide down the wire mesh they are considered not cataleptic. If the animals climb up and down the wire mesh they are nor cataleptic. In both situations the designation − is used.

The results are recorded in fractions: 0/5, 1/5, 2/5/, 3/5, 4/5 and 5/5, where 0, 1, 2, 3, 4 and 5 are the number of rats with designation + at the time where dose in question possessed the strongest effect within the first 6 hours.

5-HT antagonism, rat fundus strip

Rats, 150–200 g.
Krebs solution (NaCl 118, KCl 4.7, $CaCl_2$ 2.5, $MgSO_4$ 0.57, $KH_2PO_4$ 1.2, $NaHCO_3$ 25, glucose 10.1 mM) pregassed with carbogen.
5-hydroxytryptamine (5-HT).

Procedure

Rats are killed by a blow on the head and exsanguinated. The stomach fundus is removed and carefully cleaned with Krebs solution at 30° C. The fundus is then stretched over a rounded end of a plastic rod about the thickness of a pencil, whereby the longitudinal direction of the muscle fibers is visible. The fundus is halved by carefully cutting in the central line and in the direction of these fibres. Along this incision two strips with a length of 15–25 mm and with width 1.5–2.5 mm are cut, one from each half of the fundus. The mucosa is then carefully removed. A thread is attached to each end of a strip. One thread is fixed to a pin in the bottom of the organ bath and the other thread is fixed to an isotonic transducer. The strip is kept under a tone of 1.5 to 2.0 g. The recordings are displaced on a Watanabe WTR 331 Linearcorder Mark III. Concentration response curves to 5-HT are obtained by adding 5-HT to the bath in increasing concentrations (0.1 ml of $10^{-9}$M resulting in $1.0\times10^{-11}$M in the bath, 0.2 ml of $10^{-9}$M resulting in $3.0\times10^{-11}$M, 0.1 ml of $10^{-8}$M resulting in about $1\times10^{-10}$M, 0.2 ml of $10^{-8}$M resulting in about $3\times10^{-10}$M—0.2 ml of $10^{-4}$ resulting in about $3\times10^{-6}$M in the bath). Each concentration of 5-HT is allowed to exert its maximal effect (1–10 min) before the next is added. When the maximal response is reached the tissue is carefully washed. The test substance is added to the bath for 10 min. before examining its effect on a new cumulative 5-HT concentration response curve. From the control concentration effect curve the $K_m$ for 5-HT is calculated.

The results are recorded as mean percentage inhibition. Furthermore, the IC50 (the concentration which produces 50% inhibition) is calculated.

Substrate concentration for 5-HT: $1.0\times10^{-9}$M to $1.0\times10^{-8}$M.

Michaelis-Menten constant for 5-HT is estimated each time.

Some of the indenes of Formula I show especially interesting effects in 5-HT antagonism as measured in vitro on rat fundus strip.

The results obtained will appear from the following Tables 1 and 2:

3H-spiroperidol binding to rat striatal membranes (D-2 receptors)

Rats 125–200 g
0.1% Ascorbic acid (icecold) made fresh every day
50 mM Tris buffer pH 7.7 (at 25° C.) (icecold) stored in the cold
    7.38 gram Trisma ®—7.7/1
50 mM Tris buffer pH 7.5 (at 25° C.), containing 0.2% ascorbic acid
    (icecold) made fresh every day just before use
    753 mg Trisma ®—7.5
    200 mg Ascorbic acid
    in 100 ml icecold water
Ion-mix.
    300 ml 4M NaCl
    20 ml 2.5M KCl
    8 ml 2.5M CaCl$_2$
    4 ml 2.5M MgCl$_2$
    68 ml water
    stored in the cold
Mixed Tris buffer (icecold) made fresh every day just before use
    96 ml 50 mM Tris pH 7.7 (at 25° C.)
    96 ml 50 mM Tris pH 7.5 (at 25° C.) containing ascorbic acid
    8 ml ion-mix.
Whatman GF/B filters 25 mm
Spiroperidol[benzene ring-$^3$H] approximately 30 Ci/mmol
    from New England Nuclear. (Diluted daily to 5 nM in 0.1% ascorbic acid)
Ultra Turrax homogenizer Procedure Rats are killed by guillutination, exsanguinated and their brains removed. The corpora striata are dissected out and homogenized (Ultra Turrax, 10 sec.) in 100 vol (w/v) icecold 50 mM buffer pH 7.7 (at 25° C.). The homogenate is centrifuged twice at 20.000 g (13.000 rpm) for 10 min at 4° C., with rehomogenization (Ultra Turrax, 10 sec.) of the intermediate pellet in fresh buffer. The pellet is homogenized (Ultra Turrax, 10 sec.) in 200 volumes (w/v) of icecold, freshly prepared mixed Tris buffer.

Incubation tubes in triplicate receive on ice 100 μl of drugs dissolved in 0.1% ascorbic acid, 100 μl of 5 nM$^3$H-spiroperidol and 800 μl of the cold tissue suspension. The tubes are incubated at 37° C. for 10 min and rapidly filtered under vacuum through Whatman GF/B filters. The tubes are rinsed with 5 ml and thereafter the filters with 2×5 ml icecold 50 mM Tris buffer, pH 7.7 (at 25° C.). The radioactivity on the filters is determined by liquid scintillation counting after the addition of scintillation liquid (e.g. picofluor-15). The unspecific binding of $^3$H-spiroperidol is determined by incubating the samples with 10-6M (+)butaclamol.

Each series consists of 15 triple samples (3 controls, 2 containing 10-6M (+)butaclamol, and two series of test compounds in 5 concentrations).

The means of the controls and (+)butaclamol are calculated. The measured cpm are plotted against drug concentration on semilogarithmic paper, and the best fitting s-shaped curve is drawn. The IC50-values are determined as the concentrations, at which the binding is 50 percent of the total binding (in control samples) minus the unspecific binding ((+)butaclamol).

$^3$H-spiroperidol binding to rat cortical membranes (5-HT$_2$Receptors)

Rats 150–225 g
50 mM Tris buffer pH 7.7 (at 25° C.) (icecold) stored in the cold: 7.38 gram Trisma ®—7.7/1.
Ion-mix.
    300 ml 4M NaCl
    20 ml 2.5M KCl
    8 ml 2.5M CaCl$_2$
    4 ml 2.5M MgCl$_2$
    68 ml water
    stored in the cold.
Mixed Tris buffer (icecold) made fresh every day jut before use.
    192 ml 50 mM Tris pH 7.7 (at 25° C.)
    8 ml ion-mix.
$10^{-5}$M Mianserin: 3.01 mg mianserin-HCl/10 ml H$_2$O, Diluted 1:100.
$3\times10^{-6}$M Sulpiride: 3.41 mg sulpiride/10 ml H$_2$O, Diluted 0.3 ml to 100 ml.
Whatman GF/B filters 25 mm.
Spiroperidol[benzene ring—$^3$H—] approx. 30 Ci/mmol from New England Nuclear
    (Diluted daily to 5 nM in $3\times10^{-6}$M sulpiride solution).
Ultra Turrax homogenizer.

Procedure

Rats are killed by guillutination, exsanguinated and their brains removed. Whole cortex is dissected out and homogenized (Ultra Turrax, 10 sec.) in 100 vol (w/v) icecold 50 mM buffer pH 7.7 (at 25° C.). The homogenate is centrifuged twice at 20.000 g (13.000 rpm) for 10 min. at 4° C., with rehomogenization (Ultra Turrax, 10 sec.) of the intermediate pellet in fresh buffer. The pellet is homogenized (Ultra Turrax, 10 sec.) in 80 volumes (w/v) of icecold, freshly prepared mixed Tris buffer.

Incubation tubes in triplicate receive on ice 100 μl of drugs dissolved in water, 100 μl of 5 nM $^3$H-spiroperidol and 800 μl of the cold membrane suspension. The tubes are incubated at 37° C. for 10 min. and rapidly filtered under vacuum through Whatman GF/B filters. The tubes are rinsed with 5 ml and thereafter the filters with 2×5 ml icecold 50 mM Tris buffer, pH 7.7 (at 25° C.). The radioactivity on the filters is determined by liquid scintillation counting after the addition of 5 ml of picofluor-15. The unspecific binding of $^3$H-spiroperidol is determined by incubating the samples with $10^{-6}$M mianserine.

Each series consist of 15–16 triple samples (3 controls, 2–3 containing $10^{-6}$ mianserine and two series of test compounds in 5 concentrations).

The means of the control samples and of the $10^{-6}$M mianserine samples are calculated. The measured cpm are plotted against drug concentration on semilograithmic paper, and the best fitting s-shaped curve drawn. The IC$_{50}$-values are determined as the concentrations, at which the binding is 50 percent of the total binding (in control samples) minus the unspecific binding (mean of $10^{-6}$ mianserine samples).

TABLE 2

| | Pharmacology of hydroxyindane intermediates | | | |
|---|---|---|---|---|
| | MePh | Catalep. | 5HT | $^3$H-Spiroperido bindings |
| Compound No. | Antag. ED50 (μmol/kg) | ED50 (μmol/kg) | rat-fundus-strip IC$_{50}$/$10^{-9}$ M (μmol/kg) | DA-2  5-HT$_2$ receptors IC$_{50}$/$10^{-9}$ M |
| Lu 19-131 | 14.8 | | | |
| Lu 19-139 | 15.6 | | | |
| Lu 19-154 | 6.2 | | 5.4 | |

The compounds of Formula I and the non-toxic acid addition salts thereof may be administered to animals such as dogs, cats, horses, sheep or the like, including human beings, both orally and parenterally, and may be used for example in the form of tablets, capsules, powders, syrups or in the form of the usual sterile solutions for injection.

Results upon administration to human beings have been very gratifying.

Most conveniently the compounds of Formula I are administered orally in unit dosage form such as tablets or capsules, each dosage unit containing a non-toxic acid addition salt of one of the said compounds in an amount of from about 0.10 to about 100 mg, most preferably, however, from about 5 to 50 mg, calculated as the free amine, the total daily dosage usually ranging

TABLE 1

| | Pharmacology of indenes | | | | |
|---|---|---|---|---|---|
| | MePh | Catalep. | 5HT | $^3$H—Spiroperidol bindings | |
| Compound No. | Antag. ED50 (ip) (μmol/kg) | ED50 (po) (μmol/kg) | rat-fundus-strip IC$_{50}$/$10^{-9}$ M (μmol/kg) | DA-2 receptors IC$_{50}$/$10^{-9}$ M | 5-HT$_2$ receptors IC$_{50}$/$10^{-9}$ M |
| Lu 19-004 | 12.2 | 64.2 | 1100 | | |
| Lu 19-151 | 32.5 | 32.9 | 7500 | | |
| Lu 19-153 | 0.39 | 1.4 | 34 | | 4.6 |
| Lu 19-157 | 15.8 | 55.3 | 330 | | |
| Lu 19-158 | 4.2 | 26.0 | 26 | 12.0 | 2.8 |
| Lu 20-004 | 1.0 | 1.3 | 3260 | | 35.0 |
| Lu 20-008 | 0.64 | 2.3 | 16 | 8.9 | 4.0 |
| Lu 20-021 | 11.6 | | 500 | | |
| Lu 20-025 | 7.6 | 5.3 | 240 | | |
| Lu 20-028 | 0.78 | 6.2 | 200 | | |
| Lu 20-033 | 18.3 | 6.2 | 160 | | |
| Lu 20-038 | 0.89 | 3.8 | 28 | | |
| Lu 20-039 | 93.0 | >93 | 1900 | | |
| Lu 20-040 | 0.70 | 5.5 | 62 | | |
| Lu 20-041 | 0.14 | 1.6 | 85 | | |
| Lu 20-044 | 5.1 | | 280 | | |
| Lu 20-048 | 0.53 | 3.4 | 42 | | |
| Lu 20-053 | 19.5 | >94 | 69 | 83 | 31 |
| Lu 20-064 | 0.86 | 6.7 | 22 | | |
| Lu 20-071 | 1.7 | 2.0 | 1000 | | 15 |
| Lu 20-078 | 16.5 | | 120 | | |
| Lu 20-079 | 3.0 | | | | |
| Lu 20-082 | 70.9 | | 1500 | | |
| Lu 20-087 | 10.8 | | | | |
| Lu 20-099 | 5.6 | | 5000 | | |
| Lu 20-109 | 1.1 | | | | |
| Lu 21-002 | 1.7 | | | | |
| Chlorpromazine | 16.0 | 70.0 | >5000 | | |
| Fluphenazine | 0.07 | 0.55 | >5000 | 4.4 | 33.0 |
| Haloperidol | 0.11 | 1.0 | >10000 | | |
| Cis(Z)-flupentixol | 0.14 | 2.1 | 1050 | 3.2 | 13.0 |
| Ketanserin | | | >10000 | 2300 | 2.1 |
| Methiothepin | 2.5 | 2.3 | 58 | 2.6 | 6.8 | from about 1.0 to about 500 mg. The exact individual dosages as well as daily dosages in a particular case will, of course, be determined according to established medical principles under the direction of a physician.

When preparing tablets, the active ingredient is for the most part mixed with ordinary tablet adjuvants such as corn starch, potato starch, talcum, magnesium stearate, gelatine, lactose, gums, or the like.

When the compound of Formula I is an ester, preferably a decanoic acid ester, palmitic acid ester or a behenic acid ester, the composition may advantageously be an oily solution for injection, and such solutions often have a very prolonged effect when compared with the corresponding unesterified compound.

Typical examples of formulas for composition containing 3-(4'-fluorophenyl)-1-(1-hydroxyethyl-4-piperidyl)-6-methyl-1-indene (called Lu 20-008) for short) as the active ingredient, are as follows:

(1) Tablets containing 5 milligrams of Lu 20-008 calculated as the free base:

| | |
|---|---|
| Lu-20-008 | 5 mg |
| Lactose | 18 mg |
| Potato starch | 27 mg |
| Saccharose | 58 mg |
| Sorbitol | 3 mg |
| Talcum | 5 mg |
| Gelatine | 2 mg |
| Providone | 1 mg |
| Magnesium stearate | 0.5 mg |

(2) Tablets containing 50 mg milligrams of Lu 20-008 calculated as the free base:

| | |
|---|---|
| Lu 20-008 | 50 mg |
| Lactose | 16 mg |
| Potato starch | 45 mg |
| Saccharose | 106 mg |
| Sorbitol | 6 mg |
| Talcum | 9 mg |
| Gelatine | 4 mg |
| Providone | 3 mg |
| Magnesium stearate | 0.6 mg |

(3) Syrup containing per milliliter:

| | |
|---|---|
| Lu 20-008 | 10 mg |
| Sorbitol | 500 mg |
| Tragacanth | 7 mg |
| Glycerol | 50 mg |
| Methyl-paraben | 1 mg |
| Propyl-paraben | 0.1 mg |
| Ethanol | 0.005 ml |
| Water | ad 1 ml |

(4) Solution for injection containing per milliliter:

| | |
|---|---|
| Lu 20-008 | 50 mg |
| Acetic acid | 17.9 mg |
| Sterile water | ad 1 ml |

(5) Solution for injection containing pr milliliter:

| | |
|---|---|
| Lu 20-008 | 10 mg |
| Sorbitol | 42.9 mg |
| Acetic acid | 0.63 mg |
| Sodium hydroxide | 22 mg |

| | |
|---|---|
| -continued | |
| Sterile water | ad 1 ml |

Any other pharmaceutical tableting adjuvants may be used provided that they are compatible with the active ingredient, and additional compositions and dosage forms may be similar to those presently used for neuroleptics, such as thiothixene, clopenthixol or flupenthixol.

Also combinations of the compounds of Formula I as well as their non-toxic acid salts with other active ingredients, especially other neuroleptics, thymoleptics, tranquilizers, analgetics or the like, fall within the scope of the present invention.

As previously stated, when isolating the compounds of Formula I in the form of an acid addition salt the acid is preferably selected so as to contain an anion which is non-toxic and pharmacologically acceptable, at least in usual therapeutic doses. Representative salts which are included in this preferred group are the hydrochlorides, hydrobromides, sulphates, acetates, phosphates, nitrates, methanesulphonates, ethanesulphonates, lactates, citrates, tartrates or bitartrates, embonates and maleates of the amines of Formula I. Other acids are likewise suitable and may be employed if desired, for example, fumaric, benzoic, ascorbic, succinic, salicylic, bismethylenesalicylic, propionic, gluconic, malic, malonic, mandelic, cannamic, citraconic, stearic, palmitic, itaconic, glycolic, benzenesulphonic, and sulphamic acids may also be employed as acid addition saltforming acids.

When it is desired to isolate a compound of the invention in the form of the free base, this may be done according to conventional procedure as by dissolving the isolated or un-isolated salt in water, treating with a suitable alkaline material, extracting the liberated free base with a suitable organic solvent drying the extract and evaporating to dryness or fractionally distilling to effect isolation of the free basic amine.

The invention also comprises a method for the alleviation, palliation, mitigation, or inhibition of the manifestations of certain physiological-psychological anomalies of animals, including psychoses, depressions, pains or the like, by administering to a living animal body, including human beings, an adequate quantity of a compound of Formula I or a non-toxic acid addition salt thereof. An adequate quantity would be from about 0.001 mg to about 10 mg per kg of body weight in each unit dosage, and from about 0.003 milligrams to about 7 milligrams/kg of body weight per day.

It is to be understood that the invention is not limited to the exact details of operation or exact compound or compositions shown and described, as obvious modifications and equivalents will be apparent to one skilled in the art.

What I claim is:

1. (1) A compound selected from the group consisting of a 3-phenylindene-1 or 3-phenylindene-2 having the following formula:

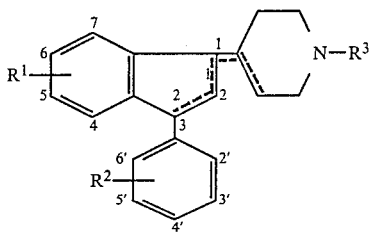

wherein the other dotted lines indicate optional bonds;

$R^1$ is selected from hydrogen, halogen, lower alkyl, lower alkoxy, hydroxymethyl, lower alkoxymethyl, cyano, trifluoromethyl, lower alkylthio and lower alkylsulfonyl;

$R^2$ is 4'-fluoro; and $R^3$ is selected from hydrogen, alkyl and alkenyl (straight or branched chain with $C_1$-$C_6$ inclusive) optionally substituted with one or two hydroxy groups, any hydroxy group present being optionally esterified with an aliphatic carboxylic acid having from two to twenty-four carbon atoms inclusive, and the group

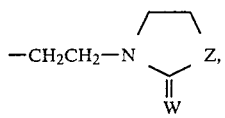

wherein Z is selected from $NR^4$, O and S, where $R^4$ is selected from H and lower alkyl, and W is selected from O and S, and (2) a pharmaceutically acceptable acid addition salt thereof.

2. A compound according to claim 1, wherein $R^1$ is selected from fluorine, $CF_3$, chlorine and methyl in the 6-position, $R^2$ is fluorine in the 4'-position, and $R^3$ is selected from methyl, 2-hydroxyethyl and

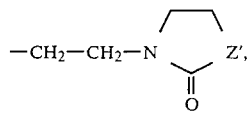

where Z' is selected from NH and O.

3. Compound of claim 1 which is 3-(4'-Fluorophenyl)-1-(1-hydroxyethyl-1,2,3,6-tetrahydropyrid-4-yl)-6-methyl-1-indene or a pharmaceutically acceptable acid addition salt thereof.

4. Compound of claim 1 which is 3-(4'-Fluorophenyl)-1-(1-hydroxyethyl-4-piperidyl)-6-methyl-1-indene or a pharmaceutically acceptable acid addition salt thereof.

5. Compound of claim 1 which is 6-Fluoro-3-(4'-fluorophenyl)-1-(1-hydroxyethyl)-4-piperidyl)-1-indene or a pharmaceutically acceptable acid addition salt thereof.

6. Compound of claim 1 which is 6-Methyl-3-(4'-fluorophenyl)-1-(1-(2-imidazolidinon-1-ylethyl)-4-piperidyl)-1-indene or a pharmaceutically acceptable acid addition salt thereof.

7. Compound of claim 1 which is 3-(4'-Fluorophenyl)-6-trifluoromethyl-1-(1-methyl-4-piperidyl)-1-indene or a pharmaceutically acceptable acid addition salt thereof.

8. A pharmaceutical composition useful for psychic disorder treatment comprising a therapeutically effective amount of a compound of claim 1 or 2 together with a pharmaceutical carrier or excipient.

9. A pharmaceutical composition according to claim 8, wherein the active ingredient is present in an amount of from 0.1–100 milligrams per unit dose.

10. A compound of the formula:

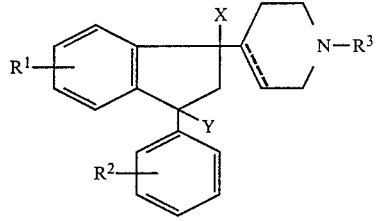

wherein $R^1$, $R^2$ and $R^3$ are as defined in claim 1, and X and Y are selected from hydrogen and hydroxy, at least one of X or Y being a hydroxy group.

11. A method for the treatment of psychic disorders in warm-blooded animals, including human beings, by administering an effective quantity of a compound of claim 1 or 2.

12. A method according to claim 11, which comprises administering the compound as a pharmaceutical composition in unit dosage form in a quantity of from 0.001 mg to 10 mg per kg of body weight.

* * * * *

UNITED STATES PATENT AND TRADEMARK OFFICE
CERTIFICATE OF CORRECTION

PATENT NO. : 4,525,360

DATED : June 25, 1985

INVENTOR(S) : Jens K. Perregaard

It is certified that error appears in the above-identified patent and that said Letters Patent is hereby corrected as shown below:

Col. 1, line 8; "3-phenylidene-2" should read -- 3-phenylindene-2 --

Col. 9, line 11; "h-hexane" should read -- n-hexane --
Col. 9, lines 61 & 62; "-pyrid-b 4-ylidane" should read
  ---pyrid-4-ylindane --
Col. 10, line 29; "-hyroxy-" should read -- -hydroxy- --
Col. 10, line 61; "methylidene" should read -- methylindane --
Col. 11, line 18; delete "-6-yl) "
Col. 11, line 34; "-6-fluoridane" should read -- -6-fluoroindane --
Col. 12, lines 16 & 17; insert -- ) -- after "C." and delete ")" at the
  beginning of the line
Col. 13, lines 3 & 4; insert -- ) -- after "-pyridyl" and delete ")" (line 4)
Col. 13, line 13; "dissoled" should read -- dissolved --
Col. 13, lines 23 & 24; insert -- ) -- after "-pyridyl" and delete ")" (line 24)
Col. 13, line 60; "-1-(1-hydroxyethyl)-4-" should read
  -- -1-(1-hydroxyethyl-4- --
Col. 16, line 6; ".3 X 2" should read -- .  3 X 2 -- (two spaces should be
  between the period and the 3)
Col. 16, line 45; "2/5/," should read -- 2/5, --
Col. 18, line 16; "nM$^3$H-spiroperidol" should read -- nM $^3$H-spiroperidol --

UNITED STATES PATENT AND TRADEMARK OFFICE
CERTIFICATE OF CORRECTION

PATENT NO. : 4,525,360

DATED : June 25, 1985

INVENTOR(S) : Jens K. Perregaard

It is certified that error appears in the above-identified patent and that said Letters Patent is hereby corrected as shown below:

Col. 15, line 63; "amound" should read -- amount --
Col. 16, line 16; "bee" should read -- been --
Col. 18, line 49; "jut" should read -- just --
Col. 21, line 18; delete ")" after "20-008"
Col. 24, line 8; delete ")" after "-hydroxyethyl"

Signed and Sealed this

Seventeenth Day of December 1985

[SEAL]

Attest:

DONALD J. QUIGG

Attesting Officer

Commissioner of Patents and Trademarks